(12) United States Patent
Musa

(10) Patent No.: US 6,953,862 B2
(45) Date of Patent: Oct. 11, 2005

(54) OXETANE COMPOUNDS CONTAINING STYRENIC FUNCTIONALITY

(75) Inventor: Osama M. Musa, Hillsborough, NJ (US)

(73) Assignee: National Starch and Chemical Investment Holding Corporation, New Castle, DE (US)

(*) Notice: Subject to any disclaimer, the term of this patent is extended or adjusted under 35 U.S.C. 154(b) by 124 days.

(21) Appl. No.: 10/430,086

(22) Filed: May 6, 2003

(65) Prior Publication Data

US 2004/0225071 A1 Nov. 11, 2004

(51) Int. Cl.⁷ ............................................. C07D 305/06
(52) U.S. Cl. ....................................................... 549/510
(58) Field of Search .................................. 549/510, 10

(56) References Cited

U.S. PATENT DOCUMENTS

| | | | |
|---|---|---|---|
| 3,415,794 A | * 12/1968 | Orth et al. ................. | 526/266 |
| 3,867,353 A | 2/1975 | Hsieh et al. | |
| 4,225,691 A | 9/1980 | Crivello | |
| 2002/0089067 A1 | 7/2002 | Crane et al. | |
| 2002/0143112 A1 | 10/2002 | Weinert et al. | |

FOREIGN PATENT DOCUMENTS

| | | |
|---|---|---|
| EP | 1 095 938 | 5/2001 |
| JP | 2001329112 | 11/2001 |
| WO | WO 00/18823 | 4/2000 |
| WO | WO 02/06038 02 | 1/2002 |
| WO | WO 02/06038 03 | 1/2002 |
| WO | WO 02/28985 | 4/2002 |

OTHER PUBLICATIONS

Ishizone T. et al.: "Protection and Polymerization of Functional Monomers. 29. Syntheses of Well–Defined Poly[4–vinylphenyl)acetic acid], Poly[3–(4–vinylphenyl)propionic acid], and Poly(3–vinylbenzoic acid) by Means of Anionic Living Polymerizations of Protected Monomers Bearing Bicyclic Ortho Ester Moieties"; Macromolecules 1999, 32, 1453–1462.

Motoi M. et al.: "Preparation of Polyoxetane–Polystyrene Composite Resins and Their Use as Polymeric Supports of Phase–Transfer Catalysts"; Poly. Journal, vol. 21, No. 12, pp 987–1001 (1989).

Glarvey P. et al.: "Conjugated Reactive Mesogens For Organo–Electronic Devices"; Polymer Preprints 2003, 44 (2),346; U.K.

Ledwith, Anthony: "Possibilities for promoting cationic polymerization by common sources of free radicals"; *Polymer 1978*, vol. 19; Oct.; pp. 1217–1222.

Sasaki, Hiroshi et al.: "Photoinitiated Cationic Polymerization of Oxetane Formulated with Oxirane"; *Journal of Polymer Science Part A*; vol. 33; 1995; pp. 1807–1816.

Searles, Scott et al.: "Hydrogen Bonding Ability and Structure of Ethylene Oxides"; *This Journal*;73;3704;1951.

Xianming, Hu et al.: "Phase–Transfer Synthesis of Optically Pure Oxetanes Obtained from 1,2,2–Trisubstituted 1,3–Propanediols"; *Synthesis May 1995*; pp. 533–538.

Fujiwara, Tomoko et al.: "Synthesis and Characterization of Novel Oxetane Macromonomers"; *Polymer Preprints 2003*; 44(1), 785.

Dhavalikar, R. et al.: "Molecular and Structural Analysis of a Triepoxide–Modified Poly(ethylene terephthalate) from Rheological Data"; *Journal of Polymer Science*: Part A: Polymer Chemistry; vol. 41, 958–969 (2003); pp. 958–969.

Satoh, Toshifumi et al.: "A Novel Ladder Polymer. Two–Step Polymerization of Oxetanyl Oxirane Leading to a "Fused 15–Crown–4 Polymer" Having a High Li* –Binding Ability"; *Macromolecules 2003*, 36, 1522–1525.

Chen, Yu et al.: "Synthesis of Multihydroxyl Branched Polyethers by Cationic Copolymerization of 3,3–Bis(hydroxymethyl)oxetane and 3–Ethyl–3–(hydroxymethyl)oxetane"; *Journal of Polymer Science*: Part A: Polymer Chemistry, vol. 40, 1991–2002; 2002 Wiley Periodicals, Inc.

Nishimura, Tomonari et al.: "Chemoselective isomerization of amide–substituted oxetanes with Lewis acid to give oxazine derivatives or bicyclic amide acetals"; *Chem. Commun., 1998*; pp. 43–44.

Miwa, Yoshiyuki et al.: "Polymerization of Bis–Oxetanes Consisting of Oligo–Ethylene Oxide Chain with Lithium Salts as Initiators"; Polym. J., vol 33, No. 8, 2001; pp. 568–574.

(Continued)

Primary Examiner—Bernard Dentz
(74) Attorney, Agent, or Firm—Jane E. Gennaro

(57) ABSTRACT

These compounds contain an oxetane functionality and a styrenic functionality. The oxetane functionality is homopolymerizable in reactions that undergo cationic or anionic ring opening, and the styrenic is polymerizable with compounds such as electron acceptor compounds. The dual functionality allows for dual cure processing. The compounds will have the structure

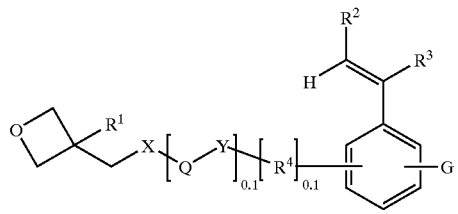

in which $R^1$ is a methyl or ethyl group; $R^2$ and $R^3$ are H or a methyl or ethyl group; $R^4$ is a direct bond or a divalent hydrocarbon; X and Y are independently a direct bond or an ether, ester, amide, or carbamate group, provided both X and Y are not a direct bond; Q is a divalent hydrocarbon (which may contain heteroatoms of N, O, or S); and G is $-OR^1$, $-SR^1$, or $-N(R^2)(R^3)$, in which $R^1$, $R^2$ and $R^3$ are as described above.

1 Claim, No Drawings

OTHER PUBLICATIONS

Ichikawa, Eiko et al.: "Synthesis of Oxetanocin A and Related Unusual Nucleosides with Bis(hydroxymethyl)–branched Sugars"; *Synthesis 2002*, No. 1, Dec. 28, 2001; Georg Thieme Verlag Stuttgart, NY; pp. 1–28.

Minegishi, Shouji et al.: "Synthesis of Polyphosphonates Containing Pendant Chloromethyl Groups by the Polyaddition of Bis(oxetanes)s with Phosphonic Dichlorides"; *Journal of Polymer Science:* Part A: Polymer Chemistry, vol. 40 3835–3846; 2002 Wiley Periodicals, Inc.

Sasaki, Hiroshi et al.: "Photoinitiated Cationic Polymerization of Oxetane Formulated with Oxirane"; *Journal of Polymer Science:* Part A: Polymer Chemistry, vol. 33, 1807–1816; 1995 John Wiley & Sons, Inc.

Rosenbaum, Dr. Barry et al.: "Develop Better Coatings"; *OMNOVA Solutions Inc.*, Akron, OH; pp. 1–5.

Sasaki, Hiroshi: "Application of Oxetane Monomers for UV–Curable Materials"; RadTech 2002; Tech. Conf. Proceedings; pp. 64–78.

Carter, Wells et al.: "New Oxetane Derivative Reactive Filuent for Cationic UV Cure"; *RadTech 2000*, Tech. Proceed.; pp. 641–649.

Crivello, J. V. et al.: "Diaryliodonium Salts as Thermal Initiators of Cationic Polymerization"; *Journal of Polymer Science:* Polymer Chemistry Ed, vol. 21, 97–109 (1983); John.Wiley & Sons, Inc.

Lu, Yong–Hong et al.: "Synthesis of Side–Chain Liquid Crystalline Polyoxetanes Containing 4–(Alkanyloxy)phenyl trans–4–Alkylcyclohexanoate Side Groups"; *1995 American Chem. Society*; pp. 1673–1680.

Lu, Yong–Hong et al.: "Synthesis of side–chain liquid crystalline polyoxetanes containing 4–dodecanyloxphenyl trans–4–alkylcyclohexanoate side groups"; *Polymer Bulletin 32*, 551–558 (1994); Springer Verlag.

Hsu, Li–Ling et al.: "Studies on the Synthesis and Properties of Ferroelectric Side Chain Liquid Crystalline Polyoxetanes"; *Journal of Polymer Science:* Part A: Polymer Chemistry; vol. 35, 2843–2855; (1997); John Wiley & Sons, Inc.

Kawakami, Yusuke et al.: "Synthesis and Thermal Transition of Side–chain Liquid Crystalline Polyoxetanes Having Laterally Attached Mesogenic Group"; *Polymer International*; 0959–8103/93; Great Britain.

Kawakami, Yusuke et al.: "Synthesis of Liquid Crystalline Polymers with a Polyoxetane Main Chain"; *Macromolecules*; vol. 24, No. 16, 1991; pp. 4531–4537.

Kawakami, Yusuke et al.: "Smectic liquid crystalline polyoxetane with novel mesogenic group"; *Polymer Bulletin 25*; Springer–Verlag 1991; pp. 439–442.

Crivello, J.V. et al.: "Photoinitiated Cationic Polymerization With Multifunctional Vinyl Ether Monomers"; *Journal of Radiation Curing*, Jan. 1983; pp. 6–13.

Ishizone, Takashi et al.: "Protection and Polymerization of Functional Monomers. 29. Syntheses of Well–Defined Poly[(4–vinylphenyl)acetic acid], Poly[3–(4–vinylphenyl)propionic acid], and Poly(3–vinylbenzoic acid) by Means of Anionic Living Polymerizations of Protected Monomers Bearing Bicyclic Ortho Ester Moieties"; *Macromolecules 1999*, 32, 1453–1462.

Sato, Kazuya et al.: "New Reactive Polymer Carrying a Pendant Oxetane Ring"; *Macromolecules 1992*, 25, 1198–1199; Communications to the Editor.

Moussa, K. et al.: "Light–Induced Polymerization of New Highly Reactive Acrylic Monomers"; *Journal of Polymer Science:* Part A: Polymer Chemistry, vol. 31, 2197–2203 (1993); John Wiley & Sons, Inc.

Kawakami, Yusuke et al.: "Synthesis of Liquid Crystalline Polyoxetanes Bearing Cyanobiphenyl Mesogen and Siloxane–Containing Substituent in the Repeating Unit"; *Polymer Journal*, vol. 28, No. 10, pp 845–850 (1996).

Crivello, J. V. et al.: "Synthesis and Photopolymerization of Silicon–Containing Multifunctional Oxetane Monomers"; *J.M.S.:–Pure Appl. Chem.*, A30(2 & 3), pp. 173–187 (1993); Marcel Dekker, Inc.

Chappelow, C. C. et al.: "Photoreactivity of Vinyl Ether/ Oxirane–Based Resin Systems"; *Journal of Applied Polymer Science*; vol. 86, 314–326 (2002); Wiley Periodicals; Inc.

Toagosei Co. Ltd.: "Developing Monomers".

"Oxetane"; Copyright 2000 American Chemical Society.

Hou, Jian et al.: "Synthesis of a Star–Shaped Copolymer with a Hyperbranched Poly(3–methyl–3–oxetanemethanol) Core and Tetrahydrofuran Arms by One–Pot Copolymerization"; *Macromol. Rapid Commun.* 2002, 23, 456–459.

Xu, Jun et al.; "Study On Cationic Ring–Opening Polymerization Mechanism of 3–Ethyl–3–Hydroxymethyl Oxetane"; *J. Macromol. Sci.–Pure Appl. Chem.*, A39(5), 431–445 (2002); Marcel Dekker, Inc.

Suzuki, Hiroshi et al.: "Photo–cationic curable materials using cationic polymerizable monomers such as epoxides and vinyl ether derivatives"; *Polymer Preprints 2001*, 42(2), 733.

Kanoh, Shigeyoshi et al.: "Monomer–Isomerization Polymerization of 3–Methyl–3–(phthalimidomethyl)oxetane with Two Different Ring–Opening Courses"; *Macromolecules 1999*, 32, 2438–2448; 1999 American Chemical Society.

Jansen, Johan F.G.A. et al.: "Effect of Dipole Moment on the Maximum Rate of Photoinitiated Acrylate Polymerizations"; *Macromolecules 2002*, 35, 7529–7531; 2002 American Chemical Society; Communications to the Editor.

Crivello, J. V. et al.: "Structure And Reactivity Relationships In The Photoinitiated Cationic Polymerization Of Oxetane Monomers"; *J.M.S.–Pure Appl. Chem.*, A30(2&3), pp. 189–206 (1993); Marcel Dekker, Inc.

Machida, Shigeru et al.: "The Highly Syn–Selective Michael Reaction Of Enamines With –(1–Alkenyl)–1, 3–Dioxolan–2–Ylium Cations Generated From 2,2–Dimethoxyethyl 2–Alkenoates In Situ"; *Tetrahedron* vol. 47, No. 23, pp. 3737–3752, 1991; 1991 Pergamon Press plc.

Motoi, Masatoshi et al.: "Preparation of Polyoxetane–Polystyrene Composite Resins and Their Use as Polymeric Supports of Phase–Transfer Catalysts"; *Polymer Journal*, vol. 21, No. 12, pp 987–1001 (1989).

Pattison, Dexter B.: "Cyclic Ethers Made by Pyrolysis of Carbonate Esters"; *Orchem Laboratories* E.I. DuPont; Jan. 17, 1957.

Smith, Tara J. et al.: "Ring Opening of 2–Ethyl–2–Hydroxymethyl Oxetane Under Basic Conditions"; *Polymer Preprints 2002*, 43(2), 984.

Nishikubo, Tadatomi et al.: "Synthesis of Alternating Copolyesters of Oxetanes With Cyclic Carboxylic Anhydrides Using Quaternary Onium Salts"; *Polymer Preprints 2002*, 43(2), 1135–1136.

Amass, A. J. et al.: "Studies In Ring–Opening Polymerization–XII. The Ring–Opening Polymerization Of Oxetane To Living Polymers Using A Porphinato–Aluminum Catalyst"; *Eur. Polym. J*: vol. 30, No. 5, pp. 641–646, 1994, Elsevier Science Ltd. 1994.

Takeuchi, Daisuke et al.: "Controlled Coordinate Anionic Polymerization of Oxetane by Novel Initiating Systems: Onium Salts/Bulky Organoaluminum Diphenolates"; *Macromolecules 1996*, 29, 8096–8100.

Kanoh, Shigeyoshi et al.: "Cationic Monomer–Isomerization Polymerization of Oxetanes Having an Ester Substituent, to Give Poly(orthoester) or Polyether"; *Macromol. Chem. Phys. 2002*, 203, 511–521; Wiley–Vch.

Kanoh, Shigeyoshi et al.: "Double Isomerization of Oxetane Amides to Azetidine Esters with Ring Expansion and Contraction"; *J. Org. Chem. 2000*, 65, 2253–2256, 2000 American Chemical Society.

Kudo, Hiroto et al.: "Synthesis of a Hetero Telechelic Hyperbranched Polyether. Anionic Ring–Opening Polymerization of 3–Ethyl–3–(hydroxymethyl)oxetane Using Potassium tert –Butoxide as an Initiator"; Short Communications; *Polym. J.*, vol. 35, No. 1, 2003; pp. 88–91.

Ueyama, Akihiko et al.: "Preparation of Polyoxetane Resins Having Polyoxirane Segments in the Pendant and Cross–Linking Chains and Uses as Polymeric Solvents for Alkali–Metal Ions"; *Polymer Journal*, vol. 34, No. 12 pp 944–953 (2002).

Singha, Nikhil K. et al.: "Atom Transfer Radical Copolymerization (ATRCP) Of A Monomer Bearing An Oxetane Group"; *Polymer Preprints* 2002, 43(2), 165.

Sasaki, H. et al.: "The Synthesis, Characterization, And Photoinitiated Cationic Polymerization Of Difunctional Oxetanes"; *J.M.S.–Pure Appl. Chem.*, A29(10), pp. 915–930 (1992).

Singha, Nikhil K. et al.: "Atom Transfer Radical Copolymerization (ATRCP) Of A Monomer Bearing An Oxetane Group"; Polymer Preprints 2002, 43(2), 165.

Hsieh, H.L.: "Terpolymerization of Cyclic Ethers with Cyclic Anhydride"; J. Macromol. Sci.–Chem., A7(7), pp. 1525–1535 (1973).

Bach, Thorsten: "The Paterno–Buchi Reaction of 3–Heteroatom–Substituted Alkenes as a Stereoselective Entry to Polyfunctional Cyclic and Acyclic Molecules"; Liebigs. Ann./Recueil 1997, 1627–1634.

Bach, Thorsten: "Synthesis of syn–and anti–1,2–Amino Alcohols by Regioselective Ring Opening Reactions of cis–3–Aminooxetanes"; Tetrahedron Letters, vol. 38, No. 21, pp. 3707–3710, 1997.

Meijer, Von E.W. et al: "Chiralitat nur im angeregten Zustand"; Angew Chem., 100 (1988) Nr. 7.

* cited by examiner-

OXETANE COMPOUNDS CONTAINING STYRENIC FUNCTIONALITY

FIELD OF THE INVENTION

This invention relates to oxetane compounds containing styrenic functionality.

BACKGROUND OF THE INVENTION

Oxetanes are highly reactive cyclic ethers that can undergo both cationic and anionic ring opening homopolymerization. Styrenic compounds are capable of free radical polymerization.

SUMMARY OF THE INVENTION

This invention relates to compounds that contain an oxetane functionality and a styrenic functionality. These compounds can be homopolymerizable in reactions in which the oxetane can undergo cationic or anionic ring opening, or polymerizable with compounds such as electron acceptor compounds. The dual functionality allows for dual cure processing, both thermal cure or radiation cure. This capability makes them attractive for use in many applications, such as, adhesives, coatings, encapsulants, and composites.

DETAILED DESCRIPTION OF THE INVENTION

In one embodiment, the compounds of this invention can be represented by the formula

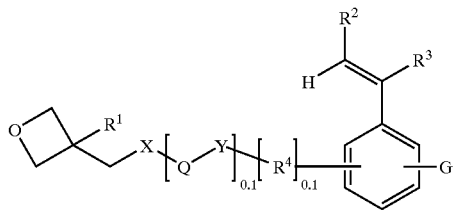

in which $R^1$ is a methyl or ethyl group; $R^2$ and $R^3$ are H or a methyl or ethyl group; $R^4$ is a direct bond or a divalent hydrocarbon; X and Y are independently a direct bond, provided both are not a direct bond, or an ether, ester, amide, or carbamate group; Q is a divalent hydrocarbon (which may contain heteroatoms of N, O, or S); and G is —$OR^1$, —$SR^1$, or —$N(R^2)(R^3)$, in which $R^1$, $R^2$ and $R^3$ are as described above; provided that X will not be

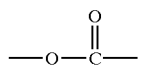

when $R^4$, Q and Y are absent, and $R^2$ and $R^3$ are H; and provided that X will not be —O— when $R^4$ is

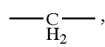

Q and Y are absent, and $R^2$ and $R^3$ are H. The configuration of the Q portion will depend on the configuration of the starting styrenic compound.

The starting styrenic compound may be small molecule, for example, 3-isopropenyl-α,α-dimethyl-benzyl isocyanate (m-TMI), 4-vinyl-benzyl chloride, the reaction product of m-TMI with a diol, the reaction product of m-TMI with the hydroxyl functionality on a carboxylic acid containing a hydroxyl group, and isoeugenol. The starting styrenic compound may also be an oligomeric or polymeric compound, prepared by reacting, for example, M-TMI or 4-vinyl-benzyl chloride with one functionality on a difunctional oligomer or polymer.

Whether the starting styrenic compound is a small molecule or an oligomeric or polymeric material, it will contain a styrenic functionality represented by the structural formula

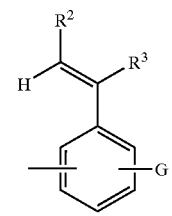

in which $R^2$ and $R^3$ are H or a methyl or ethyl group and G is —$OR^1$, —$SR^1$, or —$N(R^2)(R^3)$, in which $R^1$ is a methyl or ethyl group and $R^2$ and $R^3$ independently are H or a methyl or ethyl group. The starting styrenic compound also will contain a second functionality reactive with the starting oxetane compound. For example, the styrenic starting materials disclosed above contain halogen, hydroxyl, or isocyanato functionality in addition to the styrenic functionality.

The starting oxetane compound may be a small molecule or an oligomeric or polymeric molecule, prepared, for example, by reacting one of the small molecule oxetane starting compounds disclosed below with one functionality on a difunctional oligomer or polymer. In either case, it will contain an oxetane functionality represented by the structure

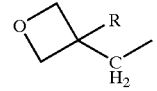

and a second functionality reactive with the second functionality on the styrenic starting compound.

Suitable starting oxetane compounds that are small molecules include, for example, (a) alcohols, such as, 3-methyl-3-hydroxymethyloxetane, 3-ethyl-3-hydroxymethyloxetane;

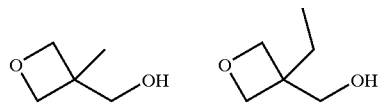

(b) halides, such as, 3-methyl-3-bromomethyloxetane, 3-ethyl-3-bromomethyloxetane, which can be prepared by the reaction of an alcohol from (a) with $CBr_4$ as is known in the art;

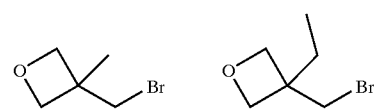

(c) alkyl halides, such as, 3-methyl-3-alkylbromomethyloxetane, 3-ethyl-3-alkylbromomethyloxetane, which can be prepared from the reaction of an alkyl dibromide compound with an oxetane alcohol from (a) as is known in the art;

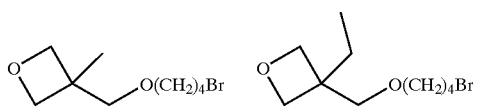

and (d) tosylates, such as, 3-methyl-3-tosylmethyloxetane, 3-ethyl-3-tosylmethyl-oxetane, which can be prepared from p-toluenesulfonyl chloride:

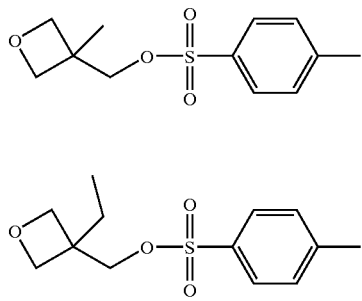

When a longer chain and higher molecular weight compound containing styrenic and oxetane is desired, either the starting styrenic compound or the starting oxetane compound, or both, may be extended by reaction with a difunctional oligomeric or polymeric material. The second functionality on this oligomeric or polymeric material must be reactive with the oxetane starting compound if the first reaction was between the styrenic starting compound and the difunctional oligomeric or polymeric material, and with the styrenic starting compound if the first reaction was between the oxetane starting compound and the difunctional oligomeric or polymeric material. Examples of suitable and commercially available oligomers and polymers include dimer diol and poly(butadiene) with terminal hydroxyl functionality.

In the case in which both the oxetane and styrenic compounds are extended by reaction with a difunctional oligomer or polymer, Q may also contain a functionality, for example, an ether, ester, carbamate, or urea functionality, resulting from the reaction of the two oligomeric or polymeric starting materials.

In general, the inventive compounds containing oxetane and styrenic functionality are prepared by reacting together a starting compound containing oxetane functionality and a second functionality and a starting compound containing styrenic functionality and a second functionality reactive with the second functionality on the oxetane compound. Typical reaction schemes include well known addition, substitution, and condensation reactions.

In a further embodiment, the compounds of this invention include polymeric compounds that contain more than one oxetane and more than one styrenic functionality. Such compounds are prepared from a polymeric starting compound from which depend functionalities that are reactive with the starting oxetane compound and the starting styrenic compound.

The polymeric compound will have the structure

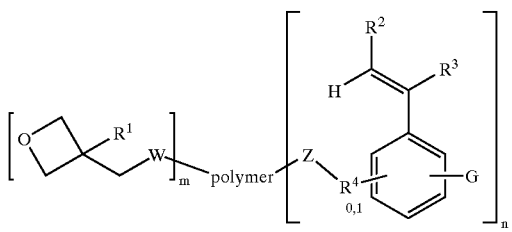

in which polymer is a polymeric backbone from which depend the oxetane and styrenic functionalities; m and n are integers that will vary with the level of oxetane and styrenic functionality added by the practitioner and typically will be from 2 to 500; $R^1$ is a methyl or ethyl group; $R^2$ and $R^3$ are H or a methyl or ethyl group; $R^4$ is a direct bond or a divalent hydrocarbon; W and Z independently are an ether, ester, amide, or carbamate group (formed through the reaction of a pendant functionality on the polymer and a corresponding reactive functionality on the starting oxetane or starting styrenic compound, respectively); and G is —$OR^1$, —$SR^1$, or —$N(R^2)(R^3)$, in which $R^1$, $R^2$ and $R^3$ are as described above.

The pendant functionalities on the polymer may be connected to the polymeric backbone by a hydrocarbon, for example, one having one to twenty carbons, that itself is dependent from the polymeric backbone. For purposes of this specification, those dependent moieties will be deemed to be part of the polymeric backbone.

An example of a commercially available and suitable polymeric backbone is poly(butadiene) having pendant hydroxyl groups. The pendant hydroxyl groups can be reacted with the oxetane starting compound containing the tosyl leaving group and with m-TMI. In this case, the linking group W will be an ether functionality and Z will contain a carbamate functionality.

As a further example, a poly(butadiene) having pendant carboxylic acid functionality can react with the hydroxyl functionality on either of the hydroxyl oxetane starting materials and with the isocyanate functionality on m-TMI. In this case, the W group will be an ester functionality and Z will contain a carbamate functionality.

Polymeric starting material can be purchased commercially, for example, there are available acrylonitrile-butadiene rubbers from Zeon Chemicals and styrene-acrylic copolymers from Johnson Polymer. The pendant functionalities from these polymers are hydroxyl or carboxylic acid functionality.

Other starting polymeric materials can be synthesized from acrylic and/or vinyl monomers using standard polymerization techniques known to those skilled in the art. Suitable acrylic monomers include α,β-unsaturated mono and dicarboxylic acids having three to five carbon atoms and acrylate ester monomers (alkyl esters of acrylic and methacrylic acid in which the alkyl groups contain one to fourteen carbon atoms). Examples are methyl acryate, methyl methacrylate, n-octyl acrylate, n-nonyl methacrylate, and their corresponding branched isomers, such as, 2-ethylhexyl acrylate. Suitable vinyl monomers include vinyl esters, vinyl ethers, vinyl halides, vinylidene halides, and nitriles of ethylenically unsaturated hydrocarbons.

Examples are vinyl acetate, acrylamide, 1-octyl acrylamide, acrylic acid, vinyl ethyl ether, vinyl chloride, vinylidene chloride, acrylonitrile, maleic anhydride, and styrene.

Other polymeric starting materials can be prepared from conjugated diene and/or vinyl monomers using standard polymerization techniques known to those skilled in the art. Suitable conjugated diene monomers include butadiene-1, 3,2-chlorobutadiene-1,3, isoprene, piperylene and conjugated hexadienes. Suitable vinyl monomers include styrene, α-methylstyrene, divinylbenzene, vinyl chloride, vinyl acetate, vinylidene chloride, methyl methacrylate, ethyl acrylate, vinylpyridine, acrylonitrile, methacrylonitrile, methacrylic acid, itaconic acid and acrylic acid.

Those skilled in the art have sufficient expertise to choose the appropriate combination of those monomers and subsequent reactions to be able to add pendant functionality, for example, hydroxyl and carboxyl functionality, for adding the oxetane and styrenic functionalities as disclosed in this specification.

EXAMPLES

Example 1
Preparation of Styrene Carbamate Ethyl Oxetane

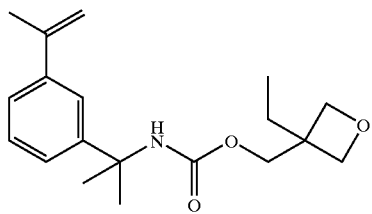

3-Ethyl-3-hydroxymethyl-oxetane (40.00 g, 0.3442 mole) and m-TMI (69.43 g, 0.3442 mole) were combined in a 250-ml four-neck round bottom flask equipped with a condenser, mechanical mixer, nitrogen purge and oil bath. The reaction was placed under nitrogen with stirring and heated to 65° C. in the oil bath. A single drop of dibutyltin dilaurate was added, thereby causing an exothermic reaction which peaked at 125° C. The oil bath was removed and the reaction temperature dropped to 65° C. within 15 minutes. At this point, the reaction was complete based on the depletion of the FT-IR isocyanate peak at 2254 cm$^{-1}$. The product was then removed from the flask as a viscous colorless liquid; however, over time it crystallized into a white solid with a m.p. of 52° C.

H$^1$-NMR: δ 7.21–7.61 (m, 4H), 5.45 (s, 1H), 5.23 (bs, 1H), 5.12 (s, 1H), 4.61–4.21 (bm, 3H), 4.05 (S, 3H), 2.15 (S, 3H), 1.55–1.85 (bm, 8H), 0.55–1.01 (bm, 3H).

Example 2
Preparation of Styrene Carbamate Methyl Oxetane

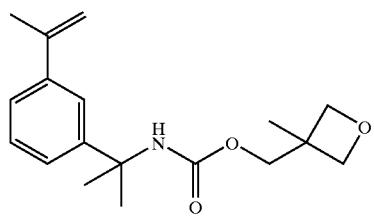

3-Methyl-3-oxetane methanol (20.00 g, 0.1958 mole) and m-TMI (39.49 g, 0.1958 mole) were combined in a 250-ml four-neck round bottom flask equipped with a condenser, mechanical mixer, thermometer, nitrogen purge and oil bath. The reaction was placed under nitrogen with stirring and heated to 65° C. in the oil bath. A single drop of dibutyltin dilaurate was added and within 5 hours the reaction was complete based on depletion of the FT-IR isocyanate peak (2254 cm$^{-1}$). The product was then removed from the flask as a colorless liquid with a viscosity of 21,000 cPs.

H$^1$-NMR: δ 7.61 (s. 1H), 7.42 (s, 3H), 5.45 (s, 1H), 5.31 (bs, 1H), 5.15 (s, 1H), 4.61 (bm, 1H), 4.39 (bm, 1H), 4.12 (s, 4H), 2.21 (s, 3H), 1.72 (bs, 6H), 0.95–1.35 (bm, 3H).

What is claimed is:

1. A compound containing oxetane and styrenic functionality having the structure

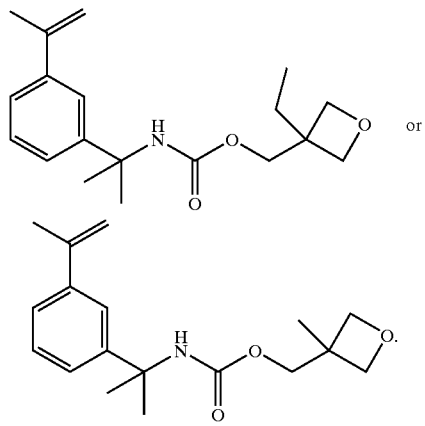

* * * * *